United States Patent [19]

Stack

[11] Patent Number: 4,966,845

[45] Date of Patent: Oct. 30, 1990

[54] MICROBIAL PRODUCTION OF L-ALTROSE

[75] Inventor: Robert J. Stack, Peoria, Ill.

[73] Assignee: The United States of America as represented by the Secretary of Agriculture, Washington, D.C.

[21] Appl. No.: 159,995

[22] Filed: Feb. 24, 1988

[51] Int. Cl.$^5$ .................. C12P 19/02; C12P 19/26; C12N 1/20; C12N 1/22
[52] U.S. Cl. ...................................... 435/105; 435/84; 435/252.33; 435/252.1; 435/822; 435/909
[58] Field of Search ............. 435/105, 84, 253, 252.33

[56] References Cited

U.S. PATENT DOCUMENTS 4,262,032   4/1981   Levin ................................. 426/658

OTHER PUBLICATIONS

Michael A. Cotta et al., "Proteolytic Activity of the Ruminal Bacterium *Butyrivibrio fibrisolvens*", Appl. Environ. Microbiol. 52(1): 51–58 (Jul., 1986).
Robert J. Stack, "Identification of L-Altrose in the Extracellular Polysaccharide from *Butyrivibrio fibrisolvens* Strain CF3", FEMS Microbiol. Lett. 48: 83–87 (1987).
Robert J. Stack et al., "Altrose-Containing Extracellular Polysaccharides Produced by Strains of *Butyrivibrio fibrisolvens*", Abstract K–149, Abstracts of the Annual Meeting of the American Society for Microbiology, Atlanta, GA, Mar. 1–6, 1987.

*Primary Examiner*—Ronald W. Griffin
*Assistant Examiner*—Pamela S. Webber
*Attorney, Agent, or Firm*—M. Howard Silverstein; John D. Fado; Curtis P. Ribando

[57] ABSTRACT

The nonnutritive sweetener L-altrose is obtained from extracellular polysaccharides elaborated by certain strains of the bacterium *Butyrivibrio fibrisolvens* when grown on a carbohydrate-containing nutrient medium. L-altrose has not previously been found in nature.

3 Claims, No Drawings

MICROBIAL PRODUCTION OF L-ALTROSE

BACKGROUND OF THE INVENTION

1. Field of the Invention

The use of nonnutritive sweeteners has grown to unprecedented levels in recent years. Because of the controversy and emotion owing to the implied safety risk associated with their use by a large segment of the population, research has been progressing at a brisk pace to find more acceptable products. This invention relates to the production of a nonnutritive sweetener by fermentation of readily available agricultural commodities.

2. Description of the Prior Art

Traditionally, the standard for sweeteners is sucrose. The more a compound resembles sucrose, the more acceptable it is to the general public. Many substances reported to be sweet have strange, nonsucrose-like flavors. Furthermore, sweetness may coexist with other tastes such as licorice or menthol. Some compounds have a lingering bitter flavor or aftertaste, others a persistent long-acting sweet taste. Sucrose solutions have a mouthfeel that cannot readily be duplicated. In addition, sucrose adds bulk or structure to solid products such as baked goods, viscosity to beverages and syrups, and functions as a weak antimicrobial agent in jams and jellies by increasing osmotic pressure.

In U.S. Pat. No. 4,262,032, Levin teaches that L-altrose is a nonnutritive sweetener. Since L-altrose is a sample, six-carbon sugar, it would be expected to have many of the desirable characteristics of sucrose which are lacking in nonsugar sweeteners. Moreover, it would be expected to be safe for human and animal consumption. However, synthesis of this sugar, which has not previously been found in nature, requires a sequence of chemical reactions with low overall yields. Until now, there has been no report of an alternative method for L-altrose production offering promise for economically feasible commercial production.

SUMMARY OF THE INVENTION

I have now surprisingly found that L-altrose can be obtained from extracellular polysaccharides elaborated by certain strains of the bacterium *Butyrivibrio fibrisolvens*. *B. fibrisolvens* is found in the digestive tract of many higher organisms. It is frequently associated with the conversion of cellulose and other carbohydrates to assimilable nutrients in ruminant animals, as reported for example by Lewis et al. [Appl. Environ. Microbiol. 50(2): 356–363, (Aug. 1985)]. I have discovered that L-altrose can be produced by cultivating these organisms on a suitable medium, hydrolyzing the extracellular polysaccharides in the medium to produce a hydrolysate, and finally recovering the L-altrose from the hydrolysate.

In accordance with this discovery, it is an object of the invention to provide an alternative to chemical synthesis for producing L-altrose.

More particularly, it is an object of the invention to provide a method for producing L-altrose by microbial fermentation.

It is also an object of the invention to facilitate the commercial feasibility of employing L-altrose as a sweetener for foods.

Other objects and advantages of the invention will become readily apparent from the ensuing description.

DETAILED DESCRIPTION OF THE INVENTION

The *B. fibrisolvens* bacteria useful in accordance with this invention are most readily obtained from the various parts of the gastrointestinal tracts of mammals. Strains of *B. fibrisolvens* have been isolated from both ruminal and cecal contents from cattle, sheep, pigs, goats, reindeer, and other sources. The species has been described by Bryant [*Butyrivibrio*, In N. R. Krieg, ed., Bergey's Manual of Systemic Bacteriology, 9th Ed., Vol. 1, The Williams and Wilkins Company, Baltimore, Md., pp. 641–643] as an anaerobic curved rod-shaped, butyric acid-forming bacterium, which stains Gram-negatively but which apparently has a thin Gram-positive wall [Cheng et al., J. Bacteriol. 129: 1506–1512 (1977)].

The specific strains of *B. fibrisolvens* useful herein are readily identifiable by assaying *B. fibrisolvens* cultures for neutral sugar composition of the elaborated extracellular polysaccharides (EPS) by any analytical procedure known in the art. For example, if the isolate in question produces L-altrose, then analysis of EPS acid hydrolysates by thin-layer chromatography (TLC) will yield spots coincident with standard L-altrose. Likewise, the presence of L-altrose in the EPS acid hydrolysates can be determined by gas-liquid chromatography (GLC) and GLC-mass spectroscopy (GLC-MS). It appears from observations made in accordance with this invention that the only configuration of altrose produced by *B. fibrisolvens* is L-altrose. Insofar as every strain of *B. fibrisolvens* identified herein as producing L-altrose also produces 4-O-(1-carboxyethyl)-D-galactose (CEG) in the EPS, it is also possible to identify suitable altrose-producing strains by any analyses using this galactose derivative as a marker. For example, CEG-containing EPS hydrolysates analyzed by conventional alditol acetate procedures yield an acetylated lactone that has a retention time relative to glucitol hexaacetate of 2.67 when analyzed by GLC using an OV-225 column.

Of approximately 40 *B. fibrisolvens* strains characterized so far, 13 have been identified in accordance with the invention as producing EPS's comprising L-altrose. These 13 strains have been tentatively classified into two of five groups of *B. fibrisolvens* established on the basis of taxonomic characteristics, including the constituent sugar composition of the elaborated EPS's.

Group III strains (see Table II), including CF1*b*, CF2*d*, CF3, CF3*a*, CF3*c* and CF4*c*, are distinguished by glucose as the only other constituent sugar component of the EPS besides L-altrose present at a significant level, as well as by the presence of an additional carboxyethyl-substituted hexose. Trace amounts of rhamnose, galactose, and the presence of CEG are also characteristic of the EPS's of these strains.

Group II strains, which are subdivided into Type A and Type B, are lacking the carboxyethyl-substituted hexose, and are further distinguished from the Group III strains by the presence of a relatively high level of galactose and a measurable level of rhamnose in the EPS. Fucose, mannose, and glucose may also be constituents of the EPS's of these strains. Strains H4*a*, R-28, ARD-23*c*, and PI-7 are classifed as Type B because of the lower relative content of rhamnose, fucose, and mannose as compared to Type A strains C-14, PI-26 and ARD-22*a*.

All Group III strains and strains H4a and R-28 of Group II were deposited under the Budapest Treaty with the Agricultural Research Service in Peoria, Ill. The NRRL Accession Numbers assigned to these strains are summarized in Table II, below.

Minimal medium for *B. fibrisolvens* has not been defined. However, it has been shown by Lewis et al., supra, that a number of carbon sources are fermented by a variety of *B. fibrisolvens* strains. Included among these carbon sources and those which could be incorporated into a growth medium for the subject *B. fibrisolvens* strains are glucose, cellobiose, xylose, xylan, starch, sucrose, fructose, lactose, galactose, maltose, arabinose, esculin, salicin, dextrin, and inulin. Nitrogen can be supplied by any common organic and inorganic sources to include ammonia, ammonium salts, yeast extract, and the like. As with any growth medium, salts, vitamins, minerals, and other adjuvants may be added as desired.

The *B. fibrisolvens* bacteria may be grown under any convenient anaerobic conditions which promote their growth. Growth and EPS production both occur within the range of about 25° C. to about 39° C., with the preferred range being 37°-39° C. The pH should be maintained within a neutral range of about pH 6-8 and stirring is optional. Of course it is essential to minimize or completely eliminate all oxygen from the fermentation broth. It is usually desirable to continue the fermentation at least through the logarithmic phase, and it may be carried into the stationary phase.

Upon completion of the fermentation, it is preferable to separate the bacterial cells and other insoluble debris from the soluble EPS in the supernatant. Separation is readily achieved by filtration or centrifugation. Thereafter, the polysaccharide is concentrated by a dewatering step or removed from the supernatant by precipitation as known in the art. Suitable precipitation agents include quaternary ammonium detergents such as cetylpyridinium chloride.

The polysaccharide, with or without previous treatment by any of the aforementioned separation steps, must be hydrolyzed in order to recover the L-altrose. Of course, recovery of the L-altrose from the hydrolysate is facilitated if the bacterial cells have been previously removed. Hydrolysis may be achieved using any common strong mineral acid, organic acid, or, alternatively, a specific glycosidase enzyme. The neutral sugar composition of the hydrolysate will, of course, depend upon the initial structure of the EPS. The Group III strains of *B. fibrisolvens*, as previously mentioned, produce polysaccharides which are predominantly L-altrose and glucose.

Recovery of the L-altrose requires separation from the other constituents of the hydrolysate. This may be accomplished by any of a variety of techniques as within the skill of the person in the art. For example, on a laboratory scale, the L-altrose can be isolated by various chromatographic methods, including but not limited to paper chromatography, column chromatography, thin-layer chromatography, or any combination therof.

The recovered L-altrose may be used as a sweetener, either alone or in combination with other sweetening compounds, in conjunction with foods, feeds, and formulations thereof. Because the sweetness of L-altrose is comparable to that of sucrose, it can be used as a substitute for sucrose, replacing it on approximately an equal weight basis.

The following example is intended only to further illustrate the invention and is not intended to limit the scope of the invention which is defined by the claims.

EXAMPLE

All the bacterial strains were grown on the chemically defined medium of Cotta et al. [Appl. Environ. Microbiol. 52: 51-58 (1986)] shown in Table I, below. In the case of Strain CF2d, it was necessary to supplement the defined medium with 0.3% Trypticase (BBL Microbiology Systems, Cockeysville, Minn.) in order to establish growth. Cultures generally were grown in 500 ml of anaerobic medium in 1000-ml round-bottom flasks and were grown to stationary phase at 37° C. Yields of EPS, determined by the anthrone procedure [Dische, "Color Reactions of Carbohydrates," Methods in Carbohydrate Chemistry, Academic Press, Inc., New York, Whistler et al., eds., pp. 477-512 (1962)] with glucose as the standard, ranged from 100-400 mg/L, with the exception of Strain CF3, which yielded more than 500 mg/L. In general, Group III strains produced more EPS than Group II strains did.

Cells were removed from stationary phase cultures by centrifugation ($6000 \times g$; 30 min; 4° C.) and discarded. For extremely viscous cultures of the highest EPS-producing strains, complete cell removal was effected by diluting the centrifugate 1:1 with water followed by recentrifugation.

Culture supernatants were lyophilized to dryness and reconstituted in 50-100 ml of water. These reconstituted supernatants were placed in dialysis bags (MW cutoff=6000-8000, Spectrum Medical Industries, Los Angeles, Calif.), which had been boiled twice to remove contaminating polysaccharides, metals, and sulfides; and then dialyzed against 3-4 changes of 40 L of water over 3 days at 4° C. Dialysis was generally accompanied by the formation of a flocculent precipitate of proteinaceous material. Dialyzates were ultracentrifuged ($185,000 \times g$; 2.5 hr; 4° C.) to remove the precipitated protein and other insoluble materials. For most strains, the dialysis and ultracentrifugation removed 50-80% of the extracellular protein, leaving 90-100% of the carbohydrate in the supernatant. The amount of EPS was determined by the anthrone procedure (Dische, supra). Protein determinations were made according to Lowry et al. [J. Biol. Chem. 193: 265-275 (1951)] with bovine serum albumin as a standard.

The resulting supernatants from ultracentrifugation were lyophilized to dryness, and the neutral sugar composition of EPS was determined by GLC of alditol acetates prepared by the procedure of Stack [FEMS Microbiol. Lett. 48: 83-87 (1987)], using a modification of the procedure described by Albersheim et al. [Carbohyd. Res. 5: 340-345 (1967)]. Monosaccharides were also analyzed by TLC on silica gel plates as described by Stack, supra.

The composition and molar ratios of neutral sugar constituents in the EPS of each strain inferred from both alditol acetate and TLC data are presented in Table II, below. The sugar compositions of Group II EPS's are given relative to galactose; those of Group III are relative to altrose. Significant strain-to-strain variations were encountered in both the type and relative amount of components in the EPS's. All the polymers contained the new acidic sugar 4-O-(1-carboxyethyl)-D-galactose which has thus far been found only in the EPS of Butyrivibrio sp. The Group III EPS's contained an additional carboxyethyl-substituted hexose that was not present in Group II polysaccharides. The presence of these two components is simply indicated with a "+" because quantitation was not possible by the analytical methods used.

It is understood that the foregoing detailed description is given merely by way of illustration and that modification and variations may be made therein without departing from the spirit and scope of the invention.

TABLE I

| Composition of Growth Medium | |
|---|---|
| Ingredient | Medium$^a$ (amount/100 ml) |
| Glucose solution, 20% (wt/vol)$^b$ | 1.0 ml |
| Trypticase | (0.3)$^c$ |
| Mineral 1$^d$ | 4.0 ml |
| Mineral 3$^e$ | 4.0 ml |
| Volatile fatty acid solution$^d$ | 0.3 ml |
| Na$_2$S.9H$_2$O solution, 5.0% (wt/vol)$^b$ | 1.0 ml |
| Na$_2$CO$_3$ solution, 8.0% (wt/vol)$^b$ | 5.0 ml |
| Resazurin solution, 0.1% (wt/vol) | 0.1 ml |
| Hemin-naphthoquinone solution$^f$ | 1.0 ml |
| R-1 salts solution$^g$ | 0.1 ml |
| Vitamin solution$^{b,h}$ | 1.0 ml |

$^a$Prepared under CO$_2$; pH adjusted to 6.8 with KOH before autoclaving.
$^b$Prepared under N$_2$ (CO$_2$ for NaCO$_3$ solution) and added as a separate, sterile solution to cooled medium.
$^c$For strain CF2d, only.
$^d$Prepared as described by Caldwell et al. [Appl. Microbiol. 14: 794–801 (1966)].
$^e$Same as mineral 2 of Caldwell et al., supra, but with 5.58 g of Na$_2$SO$_4$ in place of (NH$_4$)SO$_4$.
$^f$Prepared as described by Gomez-Alarcon et al. [Appl. Environ. Microbiol. 44: 346–350 (1982)].
$^g$Prepared as described by Hespell et al. [Arch. Microbiol. 74: 1–8 (1970)].
$^h$Contained per 100 ml of 5 mM HEPES (N-hydroxyethylpiperazine-N'-2-ethane-sultonic acid) buffer (pH 7.5): biotin, folic acid, p-aminobenzoic acid, and cyanocobalamin (2.5 mg each) and calcium pantothenate, nicotinamide, riboflavin, thiamine hydrochloride, and pyridoxamine (20 mg each). The solution was filter sterilized (pore size, 0.22 μm) and stored in a dark container.

TABLE II

| Strain identification | Source$^a$ | NRRL number | Relative neutral sugar composition | | | | | | Acidic components$^c$ | |
|---|---|---|---|---|---|---|---|---|---|---|
| | | | Rha$^b$ | Fuc | Alt | Man | Gal | Glu | CEG$^d$ | Unknown$^e$ |
| Group II | | | | | | | | | | |
| *Type A* | | | | | | | | | | |
| C-14 | A | | 1.4 | 1.3 | 1.5 | 0.2 | 1.0 | 6.0 | + | — |
| PI-26 | C | | 2.1 | 0.6 | 0.2 | 0.7 | 1.0 | 1.9 | tr | — |
| ARD-22a | B | | 1.7 | 0.3 | 0.1 | tr | 1.0 | 1.3 | tr | — |
| *Type B* | | | | | | | | | | |
| H4a | B | B-18315 | 0.2 | 0.1 | 0.6 | — | 1.0 | 1.3 | + | — |
| R-28 | D | B-18316 | 0.2 | — | 0.5 | — | 1.0 | 1.1 | + | — |
| ARD-23c | B | | 0.2 | 0.1 | 0.9 | — | 1.0 | 2.6 | + | — |
| PI-7 | C | | 0.1 | tr | 0.3 | tr | 1.0 | 0.6 | tr | — |
| Group III | | | | | | | | | | |
| CF1b | B | B-18317 | tr | — | 1.0 | — | tr | 2.4 | + | + |
| CF2d | B | B-18318 | tr | — | 1.0 | — | tr | 3.7 | + | + |
| CF3 | B | B-18319 | tr | — | 1.0 | — | tr | 2.9 | + | + |
| CF3a | B | B-18320 | tr | — | 1.0 | — | tr | 2.9 | + | + |
| CF3c | B | B-18321 | tr | — | 1.0 | — | tr | 2.4 | + | + |
| CF4c | B | B-18322 | tr | — | 1.0 | — | tr | 2.5 | + | + |

$^a$A = M. P. Bryant, Department of Dairy Science, University of Illinois, Urbana, IL.
B = B. A. Dehority, Agricultural Research and Development Center, The Ohio State University, Wooster, OH.
C = G. P. Hazlewood, Department of Biochemistry, Agricultural Research Council, Institute of Animal Physiology, Babraham, Cambridge, England.
D = R. B. Hespell, Northern Regional Research Center, U.S. Department of Agriculture, Peoria, IL.
$^b$Rha = rhamnose, etc.
$^c$+ = present in undetermined amount; — = not found; tr = trace, defined as less than 0.1.
$^d$CEG = 4-O-(1-carboxyethyl)-D-galactose.
$^e$Carboxyethyl-substituted hexose.

I claim:

1. A process for producing L-altrose comprising:
   a. inoculating a suitable growth medium with a strain of the bacterium, *Butyrivibrio fibrisolvens*, which produces an L-altrose-containing extracellular polysaccharide;
   b. cultivating the bacterium; on the medium under conditions suitable for the growth of the bacterium;
   c. hydrolyzing the extracellular polysaccharide in the culture medium to produce a hydrolysate; and;
   d. recovering L-altrose from said hydrolysate;

2. The process as described in claim 1 wherein cells of the bacterium are separated from the culture medium prior to hydrolyzing the extracellular polysaccharide.

3. The process as described in claim 1 wherein the recovering of the L-altrose in step (d) includes separating the L-altrose from other components of the hydrolysate on a cation exchange column.

* * * * *